United States Patent [19]
Wilk

[11] Patent Number: 6,023,632
[45] Date of Patent: *Feb. 8, 2000

[54] ULTRASONIC MEDICAL SYSTEM AND ASSOCIATED METHOD

[76] Inventor: Peter J. Wilk, 185 West End Ave., New York, N.Y. 10023

[*] Notice: This patent is subject to a terminal disclaimer.

[21] Appl. No.: 08/892,955

[22] Filed: Jul. 16, 1997

[51] Int. Cl.⁷ .................................................. A61B 5/05
[52] U.S. Cl. ........................................ 600/407; 600/437
[58] Field of Search ................................. 600/407, 437, 600/459, 439; 73/627, 628

[56] References Cited

U.S. PATENT DOCUMENTS

| | | |
|---|---|---|
| 3,552,382 | 1/1971 | Mount . |
| 3,927,662 | 12/1975 | Ziedonis . |
| 4,757,820 | 7/1988 | Itoh ......................................... 600/439 |
| 5,091,893 | 2/1992 | Smith et al. . |
| 5,099,459 | 3/1992 | Smith . |
| 5,135,001 | 8/1992 | Sinofsky et al. . |
| 5,163,436 | 11/1992 | Saitoh et al. . |
| 5,167,231 | 12/1992 | Matsui . |
| 5,203,336 | 4/1993 | Iida et al. ................................ 600/463 |
| 5,394,877 | 3/1995 | Orr et al. ................................ 600/459 |
| 5,435,311 | 7/1995 | Umemura et al. ...................... 600/439 |
| 5,437,278 | 8/1995 | Wilk . |
| 5,611,343 | 3/1997 | Wilson ..................................... 600/445 |
| 5,619,999 | 4/1997 | Von Behren et al. ................... 600/437 |

*Primary Examiner*—Brian Casler
*Attorney, Agent, or Firm*—R. Neil Sudol; Henry D. Coleman

[57] ABSTRACT

A medical system incorporates a perforated flexible web conformable to a patient, at least one electroacoustic transducer attached to the web, an a-c current source being operatively connected to the transducer for energizing the transducer with an electrical signal of a pre-established ultrasonic frequency to produce a first pressure wave. At least one acoustoelectric transducer is attached to the web, while an analyzing component is operatively connected to the acoustoelectric transducer for determining three-dimensional shapes of internal organs of the patient by analyzing signals generated by the acoustoelectric transducer in response to second pressure waves produced at internal organs of the patient in response to the first pressure wave. An image of internal organic structures derived through the ultrasonic signal analysis is displayed on a video monitor for enabling direct observation of invasive diagnostic and therapeutic operations. Instruments are inserted into the patient through apertures in the flexible ultrasonic sensor web.

26 Claims, 8 Drawing Sheets

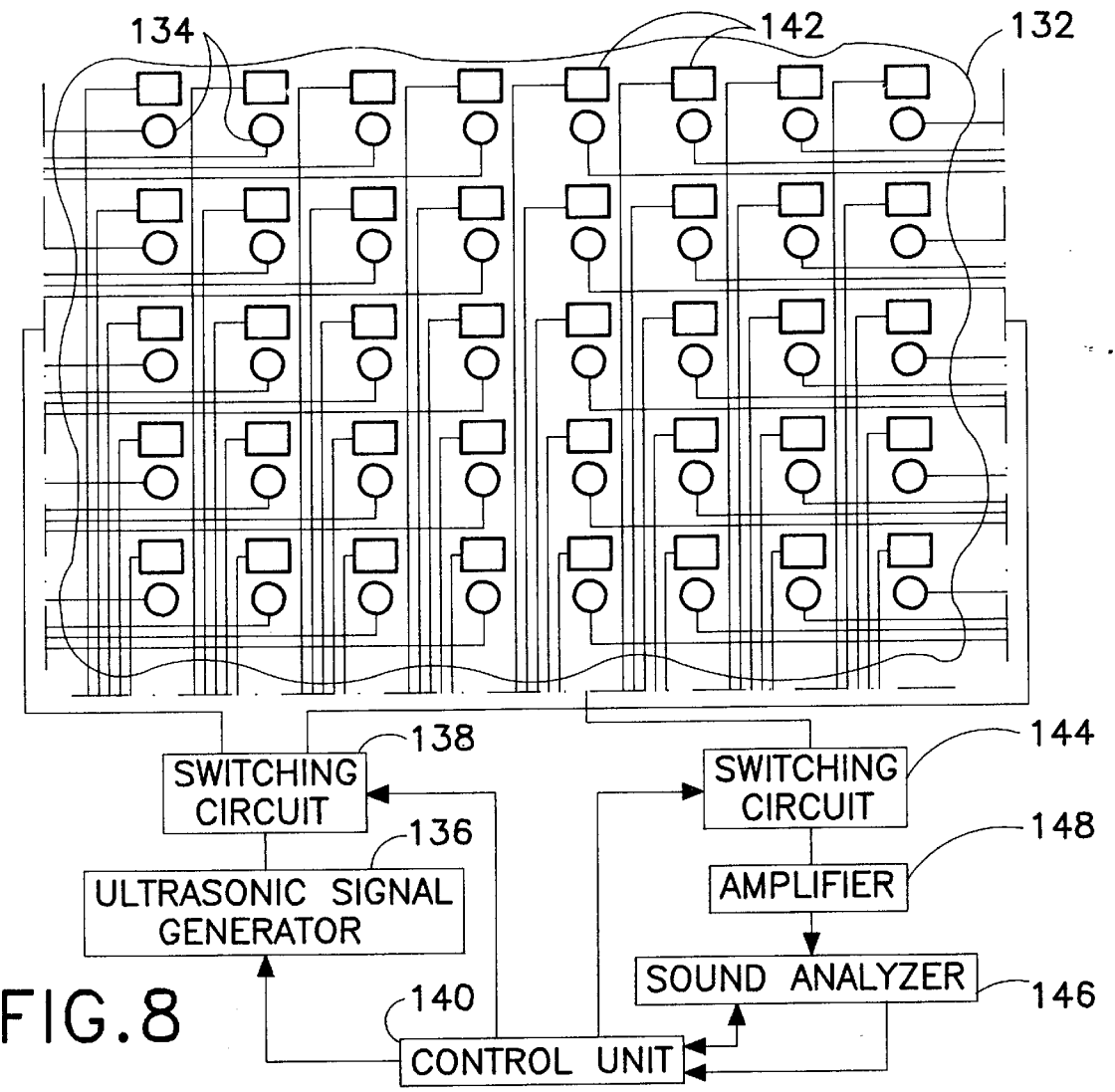

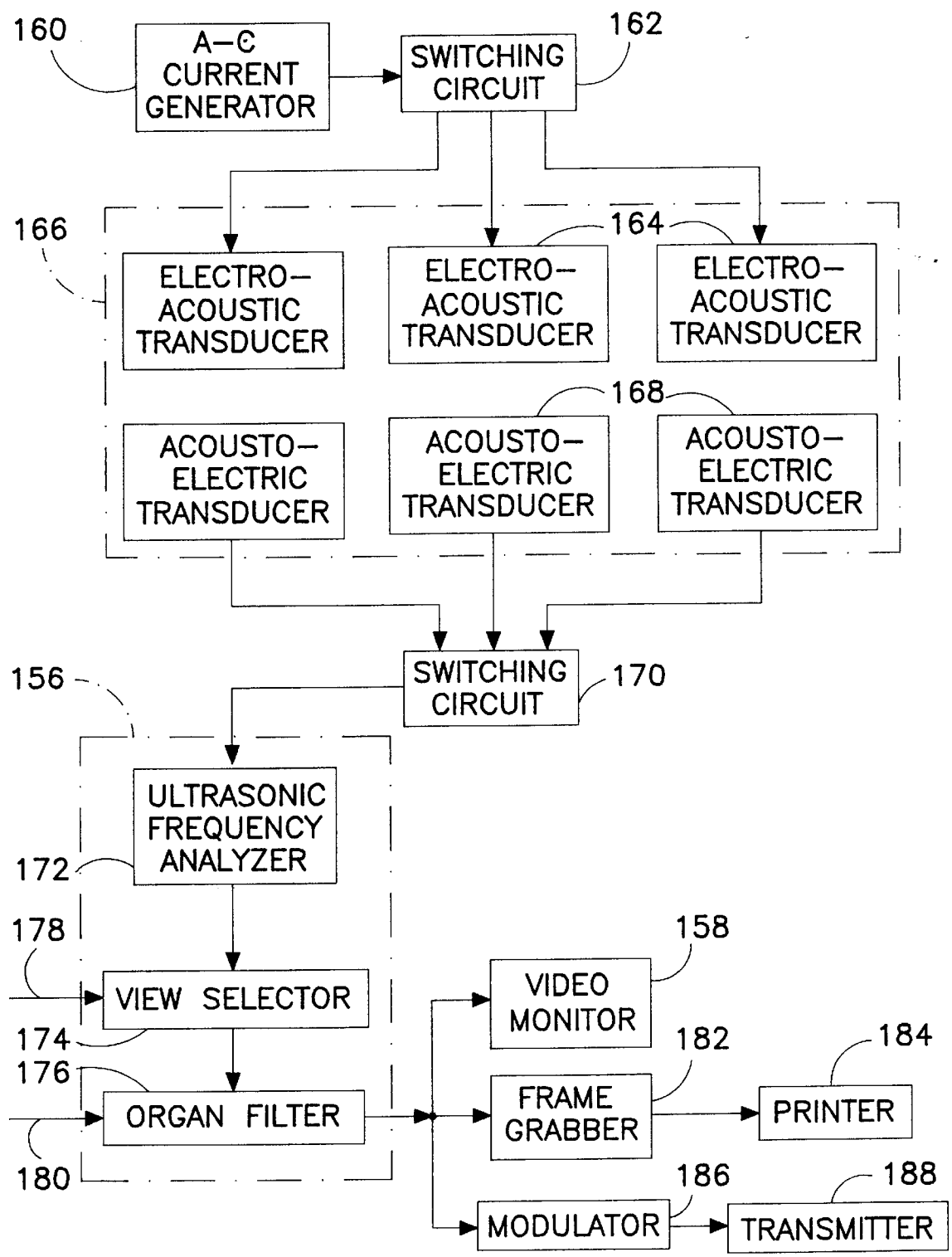

ULTRASONIC MEDICAL SYSTEM AND ASSOCIATED METHOD

BACKGROUND OF THE INVENTION

This invention relates to an ultrasonic medical system. More particularly, this invention relates to a medical system which determines three-dimensional shapes of internal organs by using ultrasonic pressure waves. This invention also relates to a method useful in medical operations.

In recent years, the escalation of medical costs has captured substantial media and regulatory attention. One reason for the escalating costs is the ever increasing use of expensive machines and testing techniques. Computed assisted tomography (CAT scanning), magnetic resonance imaging (MRI) and some radiological techniques have been in the forefront of contributing to mounting medical costs. In addition to being expensive, these devices are heavy and bulky, making them ill suited to transport.

In this age of rapidly escalating medical costs, minimally invasive operations have become the method of choice for diagnosis and treatment. In many cases, endoscopic, laparoscopic and radiographic techniques have superseded older diagnostic and therapeutic surgical techniques.

OBJECTS OF THE INVENTION

An object of the present invention is to provide an alternative to conventional medical imaging systems.

A further object of the present invention is to provide a medical imaging system which exhibits reduced costs over conventional imaging systems such as CAT scanners and MRI machines.

A particular object of the present invention is to provide a medical imaging system which can be used during the performance of so-called minimally invasive medical operations.

It is an additional object of the present invention to provide a medical imaging system which is portable.

Another object of the present invention is to provide a medical operating method which provides real time imaging in a cost effective manner.

These and other objects of the present invention will be apparent from the drawings and descriptions herein.

SUMMARY OF THE INVENTION

A medical system comprises, in accordance with the present invention, a container assembly defining a fluid- or liquid-filled chamber. The container assembly includes a flexible wall or panel which is conformable to a patient. The container assembly has at least one electroacoustic transducer in operative contact with the fluid-filled chamber so as to produce pressure waves in the fluid disposed in the chamber of the container assembly. An a-c current source is operatively connected to the transducer for energizing the transducer with an electrical signal of a pre-established ultrasonic frequency to produce a first pressure wave in the fluid in the chamber. The container assembly is further provided with at least one acoustoelectric transducer which is in operative contact with the fluid-filled chamber for detecting or picking up pressure waves in the fluid in the chamber. An analyzing component is operatively connected to the acoustoelectric transducer for determining three-dimensional shapes of internal organs of the patient by analyzing signals generated by the acoustoelectric transducer in response to second pressure waves produced at internal organs of the patient in response to the first pressure wave and transmitted through the fluid in the chamber.

Preferably, the container assembly includes a bag or bladder defining the fluid-filled chamber and further includes a plurality of substantially rigid walls or panels which partially surround and support the bag. The patient is placed on the fluid-filled bag, the upper surface of which is the flexible wall. The flexible wall deforms to receive and cradle the patient and is preferably coated with a liquid to facilitate ultrasonic pressure wave transfer between the patient and the bag.

A flexible web or sheet may be placed over the patient after disposition of the patient on the fluid-filled bag. The web or sheet may itself be provided with an ultrasonic electroacoustic and/or acoustoelectric transducer. Where the medical system is to be used in performing surgical operations under real-time visual feedback provided via ultrasonic wave generation, detection and analysis componentry, the web or cover sheet is preferably provided with a plurality of apertures enabling traversal of the web or sheet by elongate medical instruments, such as biopsy instruments or elongate instruments traditionally used in laparoscopic surgery.

According to a feature of the invention, a video monitor is linked to the analyzing component for displaying an image of the internal organs. Although stereoscopic (3-D) medical viewing systems have been introduced, it is contemplated that the image will generally be a two-dimensional image. Accordingly, the system preferentially includes a view selector operatively connected to the analyzing component and the video monitor for selecting the image from among a multiplicity of possible images of the internal organs. In addition, a filter stage may be operatively connected to the analyzing component and the video monitor for eliminating a selected organ from the image. In one example of the use of the filter, blood moving through a vessel of the vascular system is deleted to enable viewing of the blood vessel walls on the monitor.

The container assembly (optionally including the web or cover sheet) may be provided with a plurality of electroacoustic transducers disposed in a predetermined array. In that event, the system further comprises circuitry for energizing the electroacoustic transducers in a predetermined sequence. Where the container assembly has a plurality of acoustoelectric transducers disposed in a predetermined array, the system further comprises circuit components for receiving signals from the acoustoelectric transducers in a predetermined sequence.

It is contemplated generally that the transducers are disposed in or attached to the rigid walls or panels. However, the transducers may be attached to or embedded in one or more flexible walls of the fluid-filled chamber. Specifically, some of the transducers may be attached to or embedded in the flexible upper wall of the fluid-filled chamber which conforms to and engages the patient.

With the patient received by the fluid-filled bag and covered by the flexible web or sheet, ultrasonic transducers may be disposed in an array virtually surrounding the patient. This disposition of transducers provides a dense stream of organ position and configuration data to the analyzing component, thereby facilitating an enhancement of image resolution and the provision of multiple view angles.

The ultrasonic transducers may be disposed in a separate pad disposed, for example, beneath the fluid-filled bag prior to the placement of the patient on the bag.

A method for performing a medical operation, in accordance with the present invention, utilizes a medical instrument and container assembly which defines a fluid-filled chamber having a flexible wall which is conformable to a patient. The container assembly is provided with at least one electroacoustic transducer and at least one acoustoelectric transducer which are in operative contact with the fluid-filled chamber so as to respectively generate and detect ultrasonic waves in the fluid. The flexible wall of the fluid-filled chamber is disposed adjacent to a skin surface of the patient so that the chamber is in acoustic or pressure-wave-transmitting contact with the skin surface. A distal end of the medical instrument is inserted into the patient so that the distal end is disposed inside the patient while the fluid-filled chamber is disposed adjacent to the skin surface. After disposition of the container assembly adjacent to the skin surface, the electroacoustic transducer is energized with an electrical signal of a pre-established ultrasonic frequency to produce a first pressure wave in the fluid in the chamber and accordingly in the patient. Signals generated by the acoustoelectric transducer in response to second pressure waves produced at internal organs of the patient and at the distal end of the medical instrument in response to the first pressure wave are automatically analyzed to thereby determine three-dimensional shapes of the internal organs of the patient and a location of the distal end of the medical instrument relative to the internal organs, thereby enabling a real time manipulation of the instrument to effectuate a medical operation on a selected one of the internal organs.

It is contemplated that a video image will be generated of the patient's internal organs and the distal end of the medical instrument in response to the analysis of signals generated by the acoustoelectric transducer.

Preferably, the distal end of the medical instrument is inserted into the patient after the disposition of the flexible wall of the fluid-filled chamber of the container assembly in contact with the patient. Then, the insertion of the instrument into the patient can be guided in response to real-time three-dimensional structural data on the relative locations of the instrument and the internal organs of the patient.

Where a cover sheet having a plurality of apertures is placed over the patient, the medical instrument may be passed into the patient through one of the apertures. The cover sheet itself may be provided with one or more electroacoustic transducers and/or one or more acoustoelectric transducers. In this way, laparoscopic type surgery as well as other minimally invasive operations, whether diagnostic or therapeutic, may be performed with the aid of real-time visual images produced upon the analysis of returning ultrasonic pressure waves. Laparoscopic surgery is simplified by eliminating the need for a laparoscope. Laparoscope elimination enables a reduction in the number of perforations made in the patient or, alternatively, enables the insertion of another laparoscopic instrument with the same number of perforations.

Multitudinous operations are facilitated with the use of ultrasonically derived images of internal organic structures. Such operations include liver biopsies, kidney biopsies, and pleural biopsies and the placement of tubular members, including drains and catheters, for such techniques as thoracentesis and abscess drainage. Diagnostic operations now performed by using a flexible endoscope Where the container assembly has a plurality of electroacoustic transducers disposed in a predetermined array, the method further comprises energizing the electroacoustic transducers in a predetermined sequence. Where the container assembly incorporates a plurality of acoustoelectric transducers in a predetermined array, the method further comprises receiving signals from the acoustoelectric transducers in a pre-established sequence.

In accordance with an additional feature of the present invention, a printed image of the internal organs is generated in response to the analysis of signals generated by the acoustoelectric transducer. This printed image facilitates diagnosis by providing a quick and safe image.

Diagnosis is further facilitated by generating an electrical signal encoding the determined three dimensional shapes of the internal organs and wirelessly transmitting the additional signal to a remote location. Thus, consultations with experts are possible from remote locations.

It is to be noted in this regard that an ultrasonic imaging device in accordance with the present invention is portable, at least significantly more portable than conventional imaging systems such as CAT scanners and MRI machines. Thus, imaging, diagnosis and treatment is possible even where patients do not have ready access to a hospital facility. The images may be transmitted from remote locations to global medical centers where experts can view the internal structures for diagnosis and therapeutic evaluation.

A medical imaging system in accordance with the present invention enables the performance of medical operations in response to real-time visual observations of internal organic structures. This real time monitoring of invasive medical procedures is currently impossible with CAT scanners and MRI machines. An ultrasonic transducer carrier in the form of a fluid-filled container assembly is particularly well suited for minimally invasive diagnostic and therapeutic procedures. The fluid-filled bag cradles the patient in conforming contact to thereby facilitate the transmission of ultrasonic pressure waves to and from the patient. A partial embedding of the patient in the fluid-filled chamber of the container assembly facilitates the operative disposition of ultrasonic transducers all around the patient, thereby enhancing data collection, collation and analysis to generate sharper images from more angles.

BRIEF DESCRIPTION OF THE DRAWINGS

FIG. 8 is a diagram of an ultrasonography device.

FIG. 9 is a diagram showing a modification of the device of FIG. 8.

FIG. 10 is a block diagram of an ultrasonographic imaging apparatus similar to the device of FIGS. 8 and 9, for use in diagnostic and therapeutic procedures.

DESCRIPTION OF THE PREFERRED EMBODIMENTS

The present invention is directed chiefly to an ultrasonographic imaging device utilizable in diagnostic and therapeutic procedures. The ultrasonographic imaging device is described hereinafter chiefly with reference to FIG. 8 et seq. The ultrasonographic imaging device can be employed as an image generating apparatus or scanner 42 in the medical diagnostic system of FIG. 1 or a diagnostic image generating apparatus 78a, 78b, 78i in the medical diagnostic system of FIG. 4. Alternatively or additionally, the ultrasonographic imaging device can be employed in carrying out certain minimally invasive diagnostic or therapeutic operations, examples of which are illustrated schematically in FIGS. 12 and 13.

Figure 1:
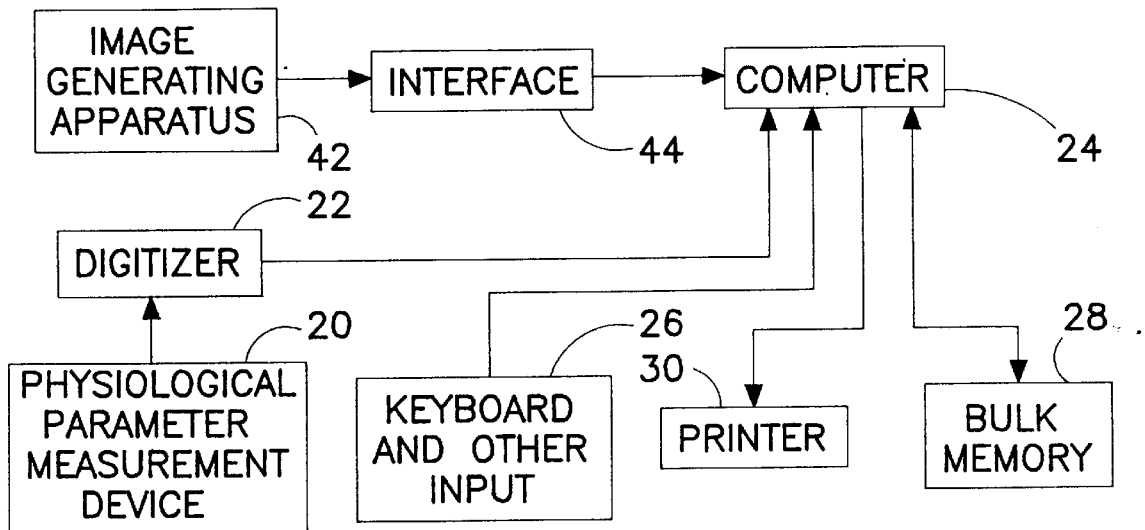
FIG. 1 is a block diagram of a medical diagnostic system, in accordance with the present invention.

As illustrated in FIG. 1, a medical diagnostic system comprises a device 20 for monitoring and measuring a biological or physiological parameter. Monitoring and measuring device 20 is juxtaposable to a patient for collecting individualized medical data about the patient's condition. Device 20 may take the form of an electronic thermometer, an electronic blood pressure gauge, a pulmonary function apparatus, a Doppler study apparatus, an EEG machine, an EKG machine, an EMG machine, or a pressure measurement device, etc., or include a plurality of such components.

Monitoring and measuring device 20 is connected at an output to a digitizer 22 which converts normally analog type signals into coded binary pulses and transmits the resulting digital measurement signal to a computer 24. Digitizer 22 may be incorporated into a housing (not shown) enclosing all or part of the monitoring and measuring device 20. Moreover, digitizer may be an integral part of monitoring and measuring device 20.

Computer 24 receives instructions and additional input from a keyboard 26. Keyboard 26 is used to feed computer 24 information for identifying the patient, for example, the patient's age, sex, weight, and known medical history and conditions. Such medical conditions may include past diseases and genetic predispositions.

Computer 24 is also connected to an external memory 28 and an output device 30 such as a printer or monitor. Memory 28 stores medical data for a multiplicity of previously diagnosed medical conditions which are detectable by analysis of data provided by monitoring and measuring device 20.

Figure 2:
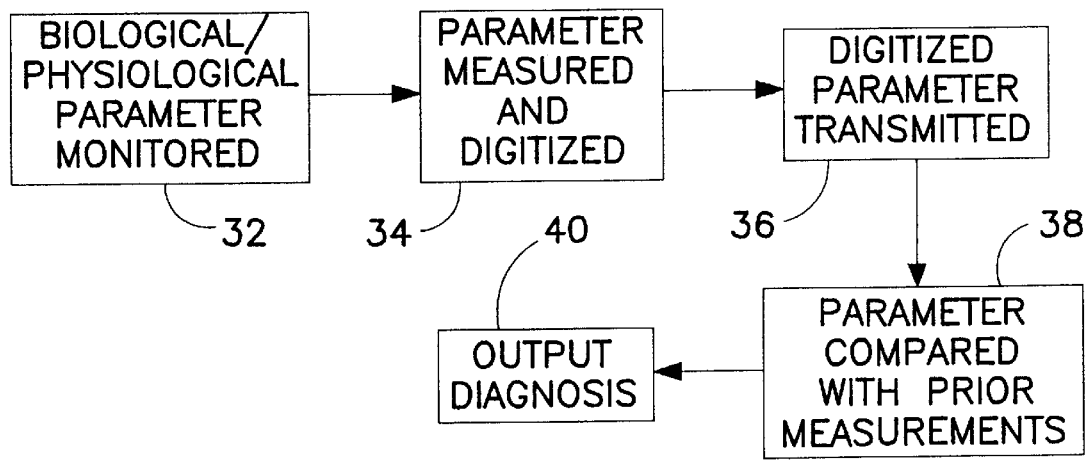
FIG. 2 is a flow-chart diagram illustrating steps in a mode of operation of the diagnostic system of FIG. 1.

As illustrated in FIG. 2, monitoring and measuring device 20 detects a magnitude of a predetermined biological or physiological parameter in a step 32. Digitizer 22 converts the detected magnitude into a pre-established digital format in a step 34 and transmits the digital signal to computer 24 in a step 36. Computer 24 is operated in a step 38 to compare the digitized data from monitoring and measuring device 20 with the data stored in memory 28 and to derive a diagnosis as to the patient's condition. The diagnosis is then communicated to the user (operator) and to the patient via output device 30 in a step 40.

If monitoring and measuring device 20 measures a physiological function characterized by a plurality of different variables, for example, the electric potential at different points on the patient's body (EEG, EKG, EMG), these variables may be broken down by computer 24 into one or more parameters, e.g., a frequency packet. The measured values of the pre-established parameters are then compared with parameter ranges stored in memory 28 for the type of parameter and the kind of patient, as characterized by sex, age, weight, etc. If the measured values of the pre-established parameters fall within expected ranges, as stored in memory 28, then computer 28 communicates a "normalcy" finding via printer 30. If, on the contrary, the measured values of one or more parameters fall outside the normal ranges, then a diagnosis of a possible medical condition is printed out.

As further illustrated in FIG. 1, the medical diagnostic system may comprise, in addition to or alternatively to monitoring and measuring device 20, image generating apparatus or scanner 42 for generating in electrically encoded form a visually readable image of an organic part of the patient. Scanner 42 may take the form of an MRI apparatus, a CAT scanner, an X-ray machine, an ultrasonography apparatus (see FIGS. 8–15), or a video camera with or without magnification optics for magnifying a sample on a slide. The video camera can be used for obtaining an image of a portion of a patient's skin.

Scanner 42 is connected via an interface 44 to computer 24.

Figure 3:
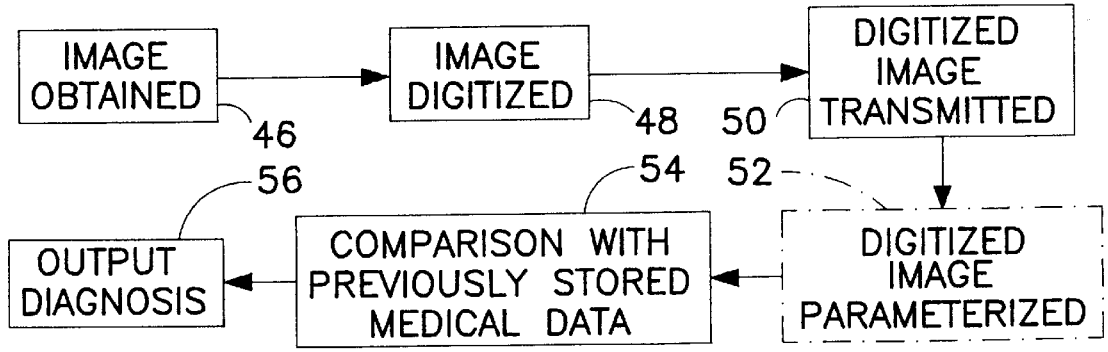
FIG. 3 is a flow-chart diagram illustrating steps in another mode of operation of the diagnostic system of FIG. 1.

As shown in FIG. 3, scanner 42 obtains an image of a tissue or organ in a step 46. The image is digitized, either by scanner 42 or interface 44 in a step 48, and is transmitted to computer 24 in a step 50. Computer 24 is operated in a step 52 to analyze the image from scanner 42 and determine specific values for a multiplicity of predetermined parameters. For example, in the event that scanner 42 takes the particular form of a video camera for dermatological diagnosis, an image of a skin surface of a patient is analyzed by computer 24 to derive such parameters as percentage of skin covered by abnormal condition, the range of sizes of individual ulcers, the range of color variation (e.g., whether bleeding is symptomatic).

The specific values of pre-established parameters calculated by computer 24 from electrically encoded images transmitted from scanner 42 are compared by computer 24 with previously determined parameter ranges stored in memory 28. For example, if a pregnant woman's fetus is being scanned by ultrasonography, the lengths of the fetal appendages, arms, legs, fingers, etc., are compared with each other and with respective fetal appendage ranges recorded in memory 28 for the stage of pregnancy, weight of the fetus, and possibly weight of the mother. In the event that any appendages are missing or are of abnormal length, a diagnosis as to possible deformity is printed out. Organs internal to the fetus may be similarly examined automatically by scanner 42 and computer 24. In more advanced stages of pregnancy, physiological functions such as the heart rate of the fetus may be automatically monitored for abnormal conditions.

The analysis performed by computer 24 on the image from scanner 42 will depend in part on the region of the patient's body being scanned. If a woman's breast or a person's cortex is being monitored for tumorous growths, computer 24 is programmed to separate the tissue image into regions of different textures. The different textured regions are parameterized as to size, shape and location and the derived parameters are compared to values in memory 30 to determine the presence of a tumor. Additional analysis is undertaken to detect lines in an image which may indicate the presence of an organic body.

A similar analysis is undertaken to evaluate a tissue specimen on a slide. The texture and line scanning may be repeated at different magnification levels if, for example, the tissue sample is a slice of an organ wall. On a high magnification level, the texture and line analysis can serve to detect microorganisms in blood.

Memory 28 may store entire images related to different diseases. For example, memory may store images of skin conditions in the event that scanner 42 takes the form of a video camera at a dermatological diagnosis and treatment facility. In a step 54 (FIG. 3), computer 24 compares the image of a patient's skin with previously stored images in memory 28, for example, by breaking down the current image into sections and overlaying the sections with sections of the stored images, at variable magnification levels.

In the event that scanner 42 takes the form of an MRI apparatus, a CAT scanner or an ultrasonographic scanner such as those described hereinafter with references to FIGS. 8–15, the images stored in memory 28 are of internal organic structures. In step 54 (FIG. 3), computer 24 compares images of a person's internal organs with previously stored organ images in memory 28. Computer 24 partitions the image from the MRI apparatus or CAT scanner into subareas and overlays the subareas with sections of the stored images, at variable magnification levels.

In a final step 40 (FIG. 3), computer 24 communicates the results of its diagnostic evaluation to a user or patient.

Figure 4:
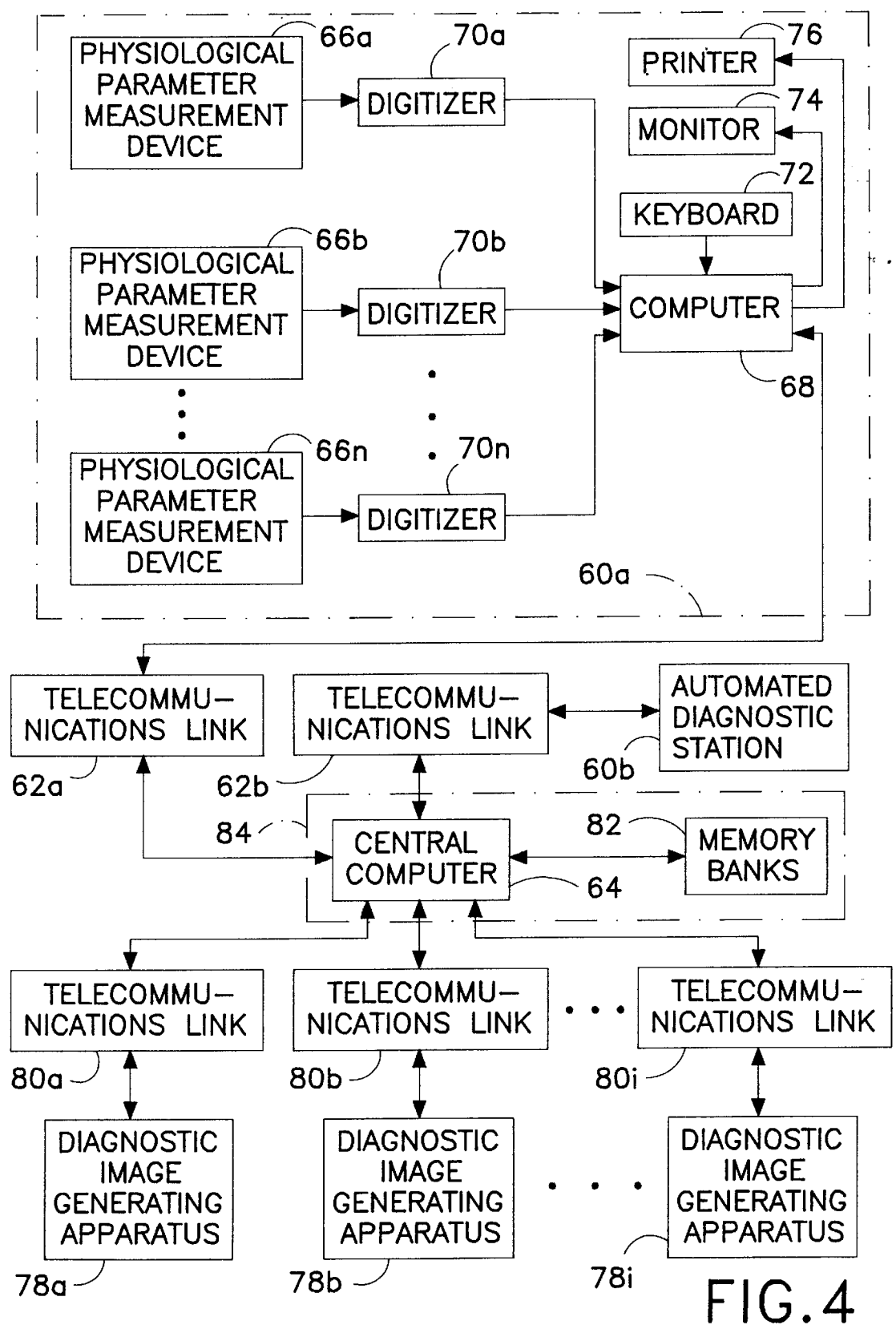
FIG. 4 a block diagram of a further medical diagnostic system.

As illustrated in FIG. 4, a medical diagnostic system comprises a plurality of remote automated diagnostic stations 60a and 60b connected via respective telecommunications links 62a and 62b to a central computer 64. Each diagnostic station 60a, 60b may take the form shown in FIG. 1, local computer 24 communicating via link 62a, 62b with central computer 64. Alternatively, each diagnostic station 60a, 60b may take the form shown in FIG. 4 and include a respective plurality of monitoring and measuring devices 66a, 66b, . . . 66n operatively connected to a local computer 68 via respective digitizer output units 70a, 70b, . . . 70n. Computer 68 is fed instructions and data from a keyboard 72 and communicates diagnostic results via a monitor 74 or printer 76. As discussed hereinabove with reference to monitoring and measuring device 20 of FIG. 1, each monitoring and measuring device 66a, 66b, . . . 66n is juxtaposable to a patient for collecting individualized medical data about the patient's condition. Monitoring and measuring devices 66a, 66b, . . . 66n may respectively take the form of an electronic thermometer, an electronic blood pressure gauge, a pulmonary function apparatus, a Doppler study apparatus, an EEG machine, an EKG machine, an EMG machine, or a pressure measurement device, etc.

Digitizers 70a, 70b, . . . 70n convert normally analog type signals into coded binary pulses and transmit the resulting digital measurement signals to computer 68. Digitizers 70a, 70b, . . . 70n may be incorporated into the housings or casing (not shown) enclosing all or part of the respective monitoring and measuring devices 66a, 66b, . . . 66n.

Keyboard 72 is used to feed computer 68 information for identifying the patient, for example, the patient's age, sex, weight, and known medical history and conditions. Such medical conditions may include past diseases and genetic predispositions.

As further illustrated in FIG. 4, a plurality of diagnostic image generating apparatuses or scanners 78a, 78b, . . . 78i are also connected to central computer 64 via respective hard-wired or wireless telecommunications links 80a, 80b, . . . 80i. Scanners 78a, 78b, . . . 78i each generate in electrically encoded form a visually readable image of an organic part of the patient. Scanners 78a, 78b, . . . 78i may each take the form of an MRI apparatus, a CAT scanner, an X-ray machine, an ultrasonography apparatus (FIGS. 8–15), or a video camera with or without magnification optics for magnifying a sample on a slide.

Because of the enormous quantity of data necessary for storing images, central computer 64 is connected to a bank of memories 82 at a central storage and information processing facility 84. Diagnosis of patient conditions may be undertaken by central computer 64 alone or in cooperation with local computers 24 or 68.

Figure 5:
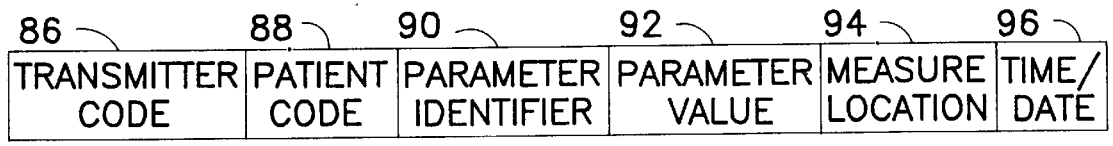
FIG. 5 is a diagram showing the composition of a data string or module used in the system of FIG. 4.

As illustrated in FIG. 5, local computers 24 and 68 transmit information to central computer 64 in data packets or modules each include a first string of binary bits 86 representing the transmitting station 60a, 60b, a second bit string 88 identifying the patient, a bit group 90 designating the parameter which is being transmitted, another bit group 92 coding the particular measured value of the parameter, a set of bits 94 identifying the point on the patient at which the measurement was taken, and another bit set 96 carrying the time and date of the measurement. Other bit codes may be added as needed.

Figure 6:
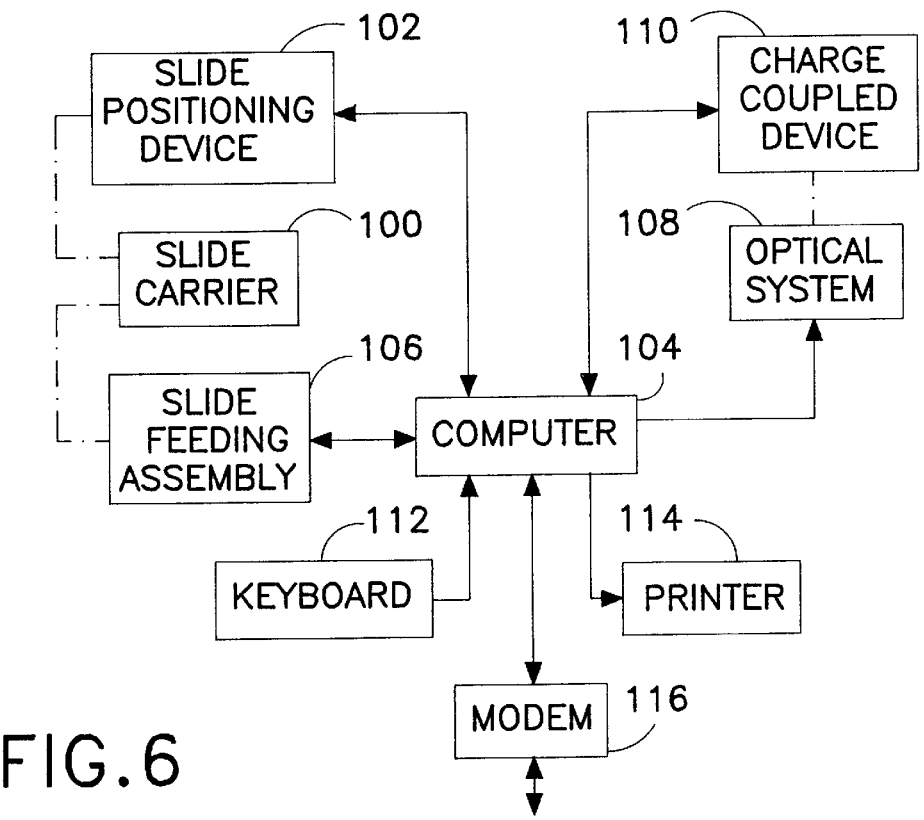
FIG. 6 is a block diagram of a computerized slide scanning system.

As shown in FIG. 6, a computerized slide scanning system comprises a slide carrier 100 mountable to a microscope stage and a slide positioning device 102 mechanically linked to the slide carrier 100 for shifting the carrier along a path determined by a computer 104. Computer 104 may be connected to an optional transport or feed assembly 106 which delivers a series of slides (not shown) successively to slide carrier 100 and removes the slides after scanning.

Computer 104 is also connected to an optical system 108 for modifying the magnification power thereof between successive slide scanning phases. Light emerging from optical system 108 is focused thereby onto a charge coupled device ("CCD") 110 connected to computer 104 for feeding digitized video images thereto.

Computer 104 performs a line and texture analysis on the digitized image information from CCD 110 to determine the presence of different organic structures and microorganisms. The different textured regions are parameterized as to size, shape and location and the derived parameters are compared to values in a memory to identify microscopic structures.

The texture and line scanning is repeated at different magnification levels.

Computer 104 may be connected to a keyboard 112, a printer 114, and a modem 16. Modem 116 forms part of a telecommunications link for connecting computer 104 to a remote data processing unit such as computer 64 in FIG. 4.

Image generating apparatus 42 in FIG. 1 may take the form of the computerized slide scanning system of FIG. 6.

Figure 7:
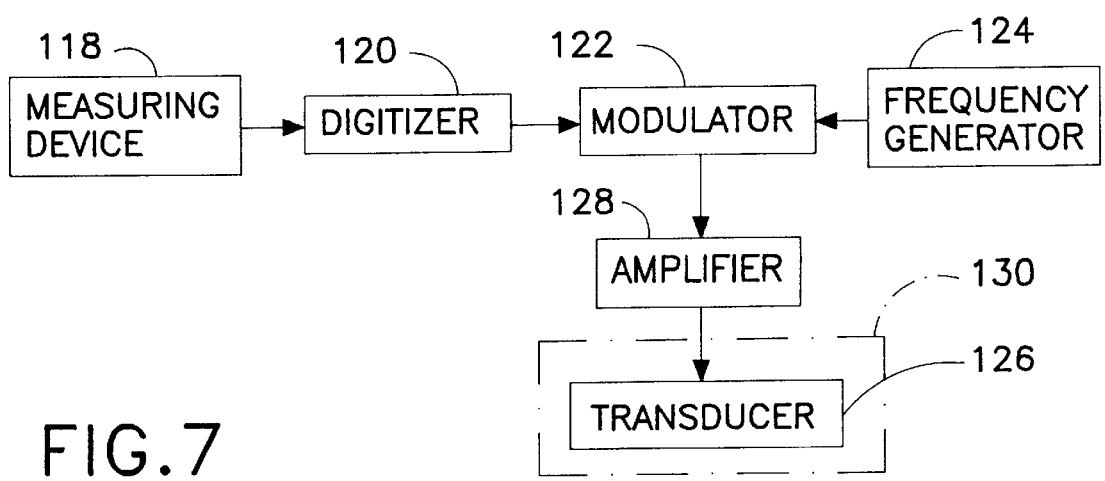
FIG. 7 is a block diagram of a device for measuring a diagnostic parameter and transmitting the measurement over the telephone lines.

As shown in FIG. 7, a device for measuring a diagnostic parameter and transmitting the measurement over the telephone lines comprises a monitoring and measuring device 118 which may take the form, for example, of an electronic thermometer, an electronic blood pressure gauge, a pulmonary function apparatus, a Doppler study apparatus, an EEG machine, an EKG machine, an EMG machine, or a pressure measurement device, etc., or include a plurality of such components. Monitoring and measuring device 118 is connected at an output to a digitizer 120 which in turn is coupled to a modulator 122. Modulator 122 modulates a carrier frequency from a frequency generator 124 with the data arriving from monitoring and measuring device 118 via digitizer 120 and transmits the modulated signal to an electroacoustic transducer 126 via an amplifier 128. Transducer 126 is removably attachable via a mounting element 130 to the mouthpiece of a telephone handset (not shown) and generates a pressure wave signal which is converted by a microphone in the handset mouthpiece back to an electrical signal for transmission over the telephone lines. Of course, transducer 126 may be omitted and modulator 122 connected directly to a telephone line.

The system of FIG. 7 enables the transmission of specialized medical data directly over the telephone lines to a central computer (e.g. computer 64 in FIG. 4) which utilizes the incoming data to perform a diagnostic evaluation on the patient.

Monitoring and measuring device 118 may include traditional medical instrumentation such as a stethoscope or modern devices such as a CCD.

FIG. 8 shows an ultrasonographic image generating apparatus which may be used in the medical diagnostic system of FIG. 1 (see reference designation 42) or in the medical diagnostic system of FIG. 4 (see reference designations 78a, 78b, . . . 78i). A flexible web 132 carries a plurality of piezoelectric electroacoustic transducers 134 in a substantially rectangular array. Transducers 134 are each connectable to an ultrasonic signal generator 136 via a switching circuit 138. Switching circuit 138 is operated by a control unit 140 to connect tranducers 134 to signal generator 136 in a predetermined sequence, depending on the area of a patient's body which is being ultrasonically scanned.

Web 132 also carries a multiplicity of acoustoelectric transducers or sensors 142 also arranged in a substantially rectangular array. Sensors 142 are connected to a switching circuit 144 also operated by control unit 140. An output of switching circuit 144 is connected to a sound or pressure wave analyzer 146 via an amplifier 148.

Web 132 is draped over or placed around a portion of a patient's body which is to be monitored ultrasonically. Control unit 140 then energizes signal generator 136 and operates switching circuit 138 to activate transducers 134 in a predetermined sequence. Depending on the transducer or combination of transducers 134 which are activated, control unit 140 operates switching circuit 144 to connect a predetermined sequence of sensors 142 to pressure wave analyzer 146. Pressure wave analyzer 146 and control unit 140 cofunction to determine three dimensional structural shapes from the echoes detected by sensors 142.

Control unit 140 is connected to ultrasonic signal generator 136 for varying the frequency of the generated signal.

FIG. 9 shows a modified ultrasonography web 150 having a limited number of electroacoustic transducers 152 and generally the same number and disposition of sensors 154 as in web 132.

Web 132 or 150 may be substantially smaller than illustrated and may corresponding carry reduced numbers of transducers 134 and 152 and sensors 142 and 154. Specifically, web 132 or 150, instead of being a sheet large enough to wrap around a torso or arm of a patient, may take a strip-like form which is periodically moved during use to different, predetermined locations on the patient. Control unit 140 and pressure wave analyzer 146 are programmed to detect internal organic structures from the data obtained at the different locations that the web 132 or 150 is juxtaposed to the patient.

FIG. 10 illustrates a modification of the ultrasonography apparatus of FIGS. 8 and 9 which is employable in diagnostic or therapeutic operations involving the insertion of an instrument into a patient. A control unit 156 for performing operations of control unit 140 is connected at an output to a video monitor 158. As discussed hereinafter with reference to FIGS. 12 and 13, a diagnostician, surgeon or other medical specialist inserts a distal end of a medical instrument into a patient in response to video feedback provided by the ultrasonography apparatus including video monitor 158.

As further illustrated in FIG. 10, an a-c current or ultrasonic signal generator 160 is connected via a switching circuit 162 to different piezoelectric type electroacoustic transducers 164 in seriatum. Transducers 162 are mounted in interspaced fashion to a flexible web 166 which also carries an array of spaced piezoelectric type acoustoelectric transducers 168.

Web is placed adjacent to a skin surface of a patient. In some cases, it may be beneficial to provide a layer of fluid between the skin surface of the patient and the web 166 to facilitate ultrasonic wave transmission from web 166 to the patient and from the patient back to the web. In response to the periodic energization of transducers 162, ultrasonic pressure waves are reflected from internal organic structures of the patient and sensed by acoustoelectric transducers 168. Electrical signals generated by transducers 168 in response to the reflected pressure waves are fed via a switching circuit 170 to control unit 156.

As discussed hereinabove with reference to control unit 140 in FIG. 8, control unit 156 controls switching circuits 162 and 170 to energize emitting transducers 164 in a predetermined sequence and and to selectively couple receiving transducers 168 in a pre-established sequence to a pressure wave or ultrasonic frequency analyzer 172 in control unit 156. The sequencing depends on the portion of the patient being monitored.

In addition to pressure wave or ultrasonic frequency analyzer 172, control unit 156 includes a view selector 174 and a filter stage 176. View selector 174 is operatively connected at an input to analyzer 172 and at an output to video monitor 158 for selecting an image for display from among a multiplicity of possible images of the internal organs detected by analyzer 172. View selector 174 may be provided with an input 178 from a keyboard (not shown) or other operator interface device for enabling an operator to select a desired view. For example, during the insertion of a medical diagnostic or treatment instrument into the patient or during manipulation of that instrument to effect an operation on a targeted internal organ of the patient, the medical practitioner may sequentially select views from different angles to optimize the practitioner's perception of the spatial relation between the distal tip of the instrument and the patient's internal organs.

Filter stage 176 is operatively connected to analyzer 172 and video monitor 158 for optionally eliminating a selected organ from the displayed image. Filter stage 176 is provided with an input 180 from a keyboard (not shown) or other operator interface device for enabling an operator to select an organ for deletion from the displayed image. In one example of the use of filter stage 176, blood moving through a vessel of the vascular system is deleted to enable viewing of the blood vessel walls on monitor 158. This deletion is easily effected starting from conventional techniques such as the Doppler detection of moving bodies.

Filter stage 176 may also function to highlight selected organs. The pattern recognition techniques discussed above are used to detect selected organs. The highlighting may be implemented exemplarily through color, intensity, cross-hatching, or outlines.

As further illustrated in FIG. 10, control unit 156 is optionally connected at an output to a frame grabber 182 for selecting a particular image for reproduction in a fixed hard copy via a printer 184. In addition, as discussed hereinabove with respect to the telecommunications links 80a, 80b . . . 80i in FIG. 4, ultrasonically derived real-time image information may be encoded by a modulator 186 onto a carrier wave sent to a remote location via a wireless transmitter 188.

Figure 11:
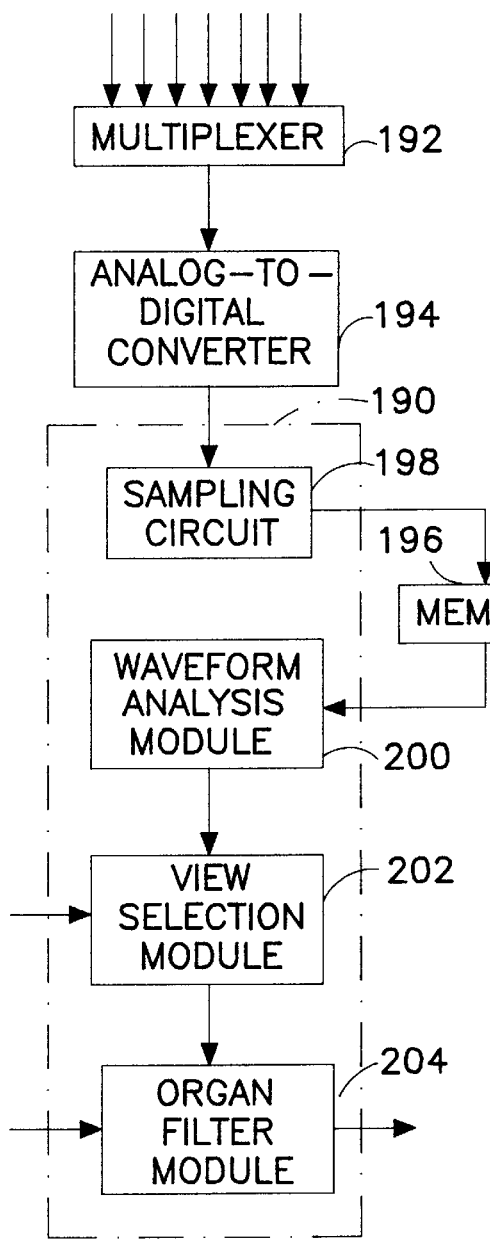
FIG. 11 is a block diagram showing a modification of the apparatus illustrated in FIG. 10.

FIG. 11 depicts the ultrasonography apparatus of FIG. 10 in a form wherein control unit 156 (FIG. 10) is realized as a specially programmed general purpose digital computer 190. A switching circuit or multiplexer 192 relays signals incoming from respective acoustoelectric transducers 168 (FIG. 10) in a predetermined intercalated sequence to an analog-to-digital converter 194, the output of which is stored in a computer memory 196 by a sampling circuit 198 of computer 190. A wave analysis module 200 of computer 190 retrieves the digital data from memory 196 and processes the data to determine three dimensional organic structures inside a patient. This three-dimensional structural data is provided to a view selection module 202 for deriving two-dimensional images for display on monitor 158 (FIG. 10). A filter module 204 is provided for removing selected organs from the image presented on the visual display or video montiro 158. Sampling circuit 198, wave analysis module 200, view selection module 202, and filter module 204 are program-modified generic digital circuits of computer 190.

Figure 12:
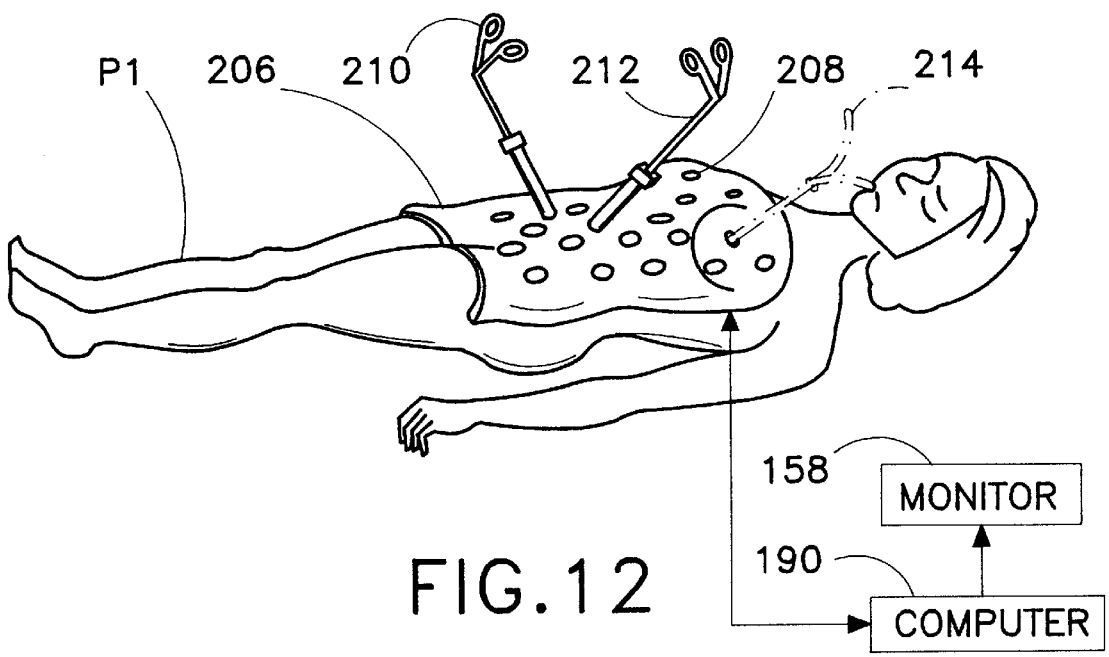
FIG. 12 is partially a schematic perspective view and partially a block diagram showing use of an ultrasonographic imaging device in a minimally invasive diagnostic or therapeutic procedure.

FIG. 12 shows a use of a flexible ultrasonic sensor web 206 which may be any of the flexible ultrasonic sensor webs described herein, except that web 206 is additionally provided with a plurality of apertures or perforations 208. Upon the placement of web 206 in pressure-wave transmitting contact with a skin surface of a patient P, elongate diagnostic or therapeutic instruments such as laparoscopic surgical instruments 210 and 212 are inserted through respective openings 208 to perform a surgical operation an a designated internal organ of the patient P1. This operation is effectuated by viewing a real time image of the distal ends of the instruments 210 and 212 in relation to the patient's internal organic structures as determined by control unit 156 or computer 190. Generally, the image on monitor 158 is viewed during insertion of instruments 210 and 212 to enable a proper employment of those instruments. Also, the video images on monitor 158 are viewed to enable a proper carrying out of the "laparoscopic" surgical operation on the designated internal organ of the patient P1. Strictly speaking, this operation is not a laparoscopic operation, since a laparoscope is not used to provide a continuing image of the patient's internal organic structures and the distal ends of instruments 210 and 212.

There are multiple advantages to using sonographic web 206 instead of a laparoscope. Fewer perforations need be made in the patient for the same number of surgical instruments. In addition, multiple views of the patient's internal organic structures are possible, rather than a single view through a laparoscope. Generally, these multiple views may differ from one another by as little as a few degrees of arc. Also, particularly if web 206 is extended essentially around patient P1, viewing angles may be from under the patient where a laparoscopic could not realistically be inserted.

Web 206 may be used to insert tubular instruments such as catheters and drainage tubes, for example, for thoracentesis and abscess drainage. The tubes or catheters are inserted through apertures 208 under direct real time observation via monitor 158.

In addition to treatment, web 206 may be used to effectuate diagnostic investigations. In particular, a biopsy instrument 214 may be inserted through an aperture 208 to perform a breast biopsy, a liver biopsy, a kidney biopsy, or a pleural biopsy.

Figure 13:
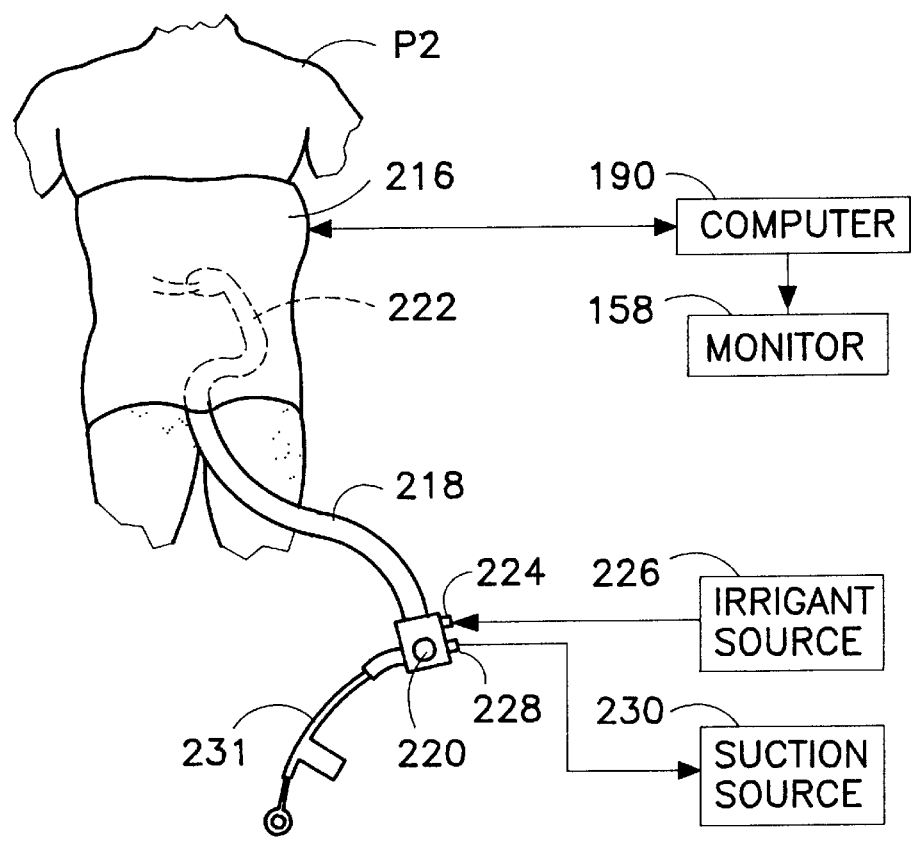
FIG. 13 is a partial schematic perspective view including a block diagram showing use of an ultrasonographic imaging device in another minimally invasive diagnostic or therapeutic procedure.

As illustrated in FIG. 13, a flexible ultrasonic sensor web 216, which may be any of the flexible ultrasonic sensor webs described herein, may be used in a diagnostic or therapeutic operation utilizing a flexible endoscope-like instrument 218. Instrument 218 has a steering control 220 for changing the orientation of a distal tip 222 of the instrument. Instrument 218 also has a port 224 connected to an irrigant source 226 and another port 228 connected to a suction source. In addition, instrument 218 is provided a biopsy channel (not shown) through which an elongate flexible biopsy instrument or surgical instrument 230 is inserted.

Instrument 218 is considerably simplified over a conventional endoscope in that instrument 218 does not require fiber-optic light guides for carrying light energy into a patient P2 and image information out of the patient. Instead, visualization of the internal tissues and organ structures of patient P2 is effectuated via monitor 158 and control unit 156 or computer 190. As discussed above with reference to FIG. 12, the sonographic imaging apparatus if web 216 is extended essentially around patient P2, images may be provided from multiple angles, not merely from the distal tip 222 of instrument 218.

View selector 174 and organ filter stage 176 or view selection module 202 and filter module 204 may function in further ways to facilitate viewing of internal organic structures. In addition to organ removal and highlighting, discussed above, a zoom capability may be provided. The zoom or mangification factor is limited only by the resolution of the imaging, which is determined in part by the frequency of the ultrasonic pressure waves.

FIG. 10 illustrates a modification of the ultrasonography apparatus of FIGS. 8 and 9 which is employable in diagnostic or therapeutic operations involving the insertion of an instrument into a patient. A control unit 156 for performing operations of control unit 140 is connected at an output to a video monitor 158. As discussed hereinafter with reference to FIGS. 12 and 13, a diagnostician, surgeon or other medical specialist inserts a distal end of a medical instrument into a patient in response to video feedback provided by the ultrasonography apparatus including video monitor 158.

As further illustrated in FIG. 10, an a-c current or ultrasonic signal generator 160 is connected via a switching circuit 162 to different piezoelectric type electroacoustic transducers 164 in seriatim. Transducers 162 are mounted in interspaced fashion to a flexible web 166 which also carries an array of spaced piezoelectric type acoustoelectric transducers 168.

Web is placed adjacent to a skin surface of a patient. In some cases, it may be beneficial to provide a layer of fluid between the skin surface of the patient and the web 166 to facilitate ultrasonic wave transmission from web 166 to the patient and from the patient back to the web. In response to the periodic energization of transducers 162, ultrasonic pressure waves are reflected from internal organic structures of the patient and sensed by acoustoelectric transducers 168. Electrical signals generated by transducers 168 in response to the reflected pressure waves are fed via a switching circuit 170 to control unit 156.

As discussed hereinabove with reference to control unit 140 in FIG. 8, control unit 156 controls switching circuits 162 and 170 to energize emitting transducers 164 in a predetermined sequence and to selectively couple receiving transducers 168 in a pre-established sequence to a pressure wave or ultrasonic frequency analyzer 172 in control unit 156. The sequencing depends on the portion of the patient being monitored.

In addition to pressure wave or ultrasonic frequency analyzer 172, control unit 156 includes a view selector 174 and a filter stage 176. View selector 174 is operatively connected at an input to analyzer 172 and at an output to video monitor 158 for selecting an image for display from among a multiplicity of possible images of the internal organs detected by analyzer 172. View selector 174 may be provided with an input 178 from a keyboard (not shown) or other operator interface device for enabling an operator to select a desired view. For example, during the insertion of a medical diagnostic or treatment instrument into the patient or during manipulation of that instrument to effect an operation on a targeted internal organ of the patient, the medical practitioner may sequentially select views from different angles to optimize the practitioner's perception of the spatial relation between the distal tip of the instrument and the patient's internal organs.

Filter stage 176 is operatively connected to analyzer 172 and video monitor 158 for optionally eliminating a selected organ from the displayed image. Filter stage 176 is provided with an input 180 from a keyboard (not shown) or other operator interface device for enabling an operator to select an organ for deletion from the displayed image. In one example of the use of filter stage 176, blood moving through a vessel of the vascular system is deleted to enable viewing of the blood vessel walls on monitor 158. This deletion is easily effected starting from conventional techniques such as the Doppler detection of moving bodies.

Filter stage 176 may also function to highlight selected organs. The pattern recognition techniques discussed above are used to detect selected organs. The highlighting may be implemented exemplarily through color, intensity, crosshatching, or outlines.

As further illustrated in FIG. 10, control unit 156 is optionally connected at an output to a frame grabber 182 for selecting a particular image for reproduction in a fixed hard copy via a printer 184. In addition, as discussed hereinabove with respect to the telecommunications links 80a, 80b . . . 80i in FIG. 4, ultrasonically derived real-time image information may be encoded by a modulator 186 onto a carrier wave sent to a remote location via a wireless transmitter 188.

FIG. 11 depicts the ultrasonography apparatus of FIG. 10 in a form wherein control unit 156 (FIG. 10) is realized as a specially programmed general purpose digital computer 190. A switching circuit or multiplexer 192 relays signals incoming from respective acoustoelectric transducers 168 (FIG. 10) in a predetermined intercalated sequence to an analog-to-digital converter 194, the output of which is stored in a computer memory 196 by a sampling circuit 198 of computer 190. A wave analysis module 200 of computer 190 retrieves the digital data from memory 196 and processes the data to determine three dimensional organic structures inside a patient. This three-dimensional structural data is provided to a view selection module 202 for deriving two-dimensional images for display on monitor 158 (FIG. 10). A filter module 204 is provided for removing selected organs from the image presented on the visual display or video monitor 158. Sampling circuit 198, wave analysis module 200, view selection module 202, and filter module 204 are program-modified generic digital circuits of computer 190.

FIG. 12 shows a use of a flexible ultrasonic sensor web 206 which may be any of the flexible ultrasonic sensor webs described herein, except that web 206 is additionally provided with a plurality of apertures or perforations 208. Upon the placement of web 206 in pressure-wave transmitting contact with a skin surface of a patient P, elongate diagnostic or therapeutic instruments such as laparoscopic surgical instruments 210 and 212 are inserted through respective openings 208 to perform a surgical operation an a designated internal organ of the patient P1. This operation is effectuated by viewing a real time image of the distal ends of the instruments 210 and 212 in relation to the patient's internal organic structures as determined by control unit 156 or computer 190. Generally, the image on monitor 158 is viewed during insertion of instruments 210 and 212 to enable a proper employment of those instruments. Also, the video images on monitor 158 are viewed to enable a proper carrying out of the "laparoscopic" surgical operation on the designated internal organ of the patient P1. Strictly speaking, this operation is not a laparoscopic operation, since a laparoscope is not used to provide a continuing image of the patient's internal organic structures and the distal ends of instruments 210 and 212.

There are multiple advantages to using sonographic web 206 instead of a laparoscope. Fewer perforations need be made in the patient for the same number of surgical instruments. In addition, multiple views of the patient's internal organic structures are possible, rather than a single view through a laparoscope. Generally, these multiple views may differ from one another by as little as a few degrees of arc. Also, particularly if web 206 is extended essentially around patient P1, viewing angles may be from under the patient where a laparoscopic could not realistically be inserted.

Web 206 may be used to insert tubular instruments such as catheters and drainage tubes, for example, for thoracentesis and abscess drainage. The tubes or catheters are inserted through apertures 208 under direct real time observation via monitor 158.

In addition to treatment, web 206 may be used to effectuate diagnostic investigations. In particular, a biopsy instrument 214 may be inserted through an aperture 208 to perform a breast biopsy, a liver biopsy, a kidney biopsy, or a pleural biopsy.

As illustrated in FIG. 13, a flexible ultrasonic sensor web 216, which may be any of the flexible ultrasonic sensor webs described herein, may be used in a diagnostic or therapeutic operation utilizing a flexible endoscope-like instrument 218.

Instrument 218 has a steering control 220 for changing the orientation of a distal tip 222 of the instrument. Instrument 218 also has a port 224 connected to an irrigant source 226 and another port 228 connected to a suction source 230. In addition, instrument 218 is provided a biopsy channel (not shown) through which an elongate flexible biopsy instrument or surgical instrument 231 is inserted.

Instrument 218 is considerably simplified over a conventional endoscope in that instrument 218 does not require fiber-optic light guides for carrying light energy into a patient P2 and image information out of the patient. Instead, visualization of the internal tissues and organ structures of patient P2 is effectuated via monitor 158 and control unit 156 or computer 190. As discussed above with reference to FIG. 12, the sonographic imaging apparatus if web 216 is extended essentially around patient P2, images may be provided from multiple angles, not merely from the distal tip 222 of instrument 218.

View selector 174 and organ filter stage 176 or view selection module 202 and filter module 204 may function in further ways to facilitate viewing of internal organic structures. In addition to organ removal and highlighting, discussed above, a zoom capability may be provided. The zoom or magnification factor is limited only by the resolution of the imaging, which is determined in part by the frequency of the ultrasonic pressure waves.

Figure 14:
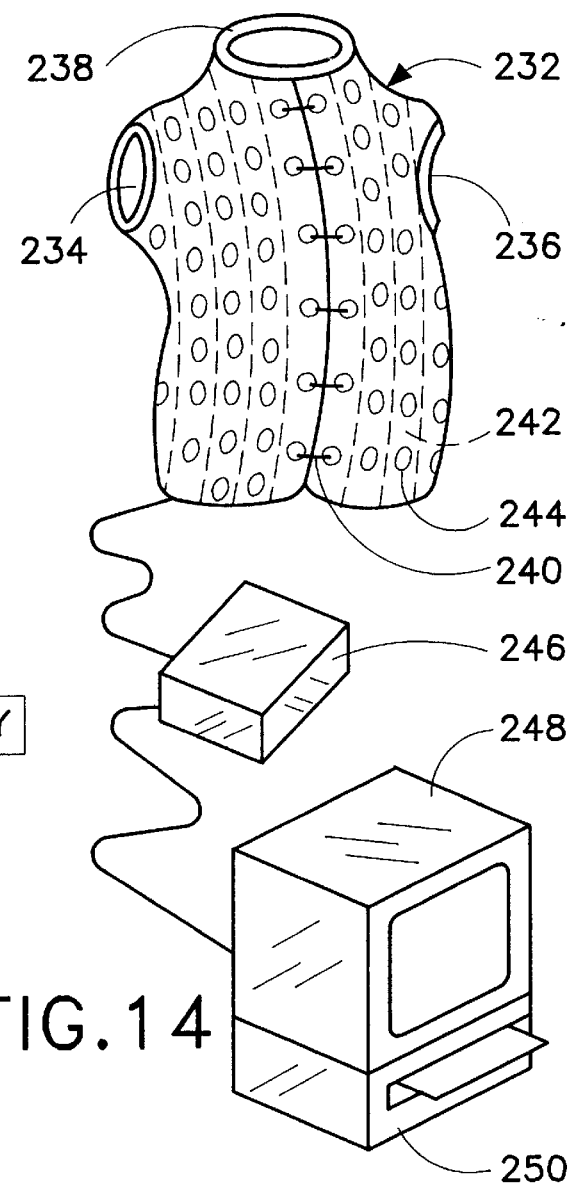
FIG. 14 is a schematic perspective view of yet another ultrasonographic imaging device in accordance with the present invention, showing a sensor vest in a closed, use configuration.
Figure 15:
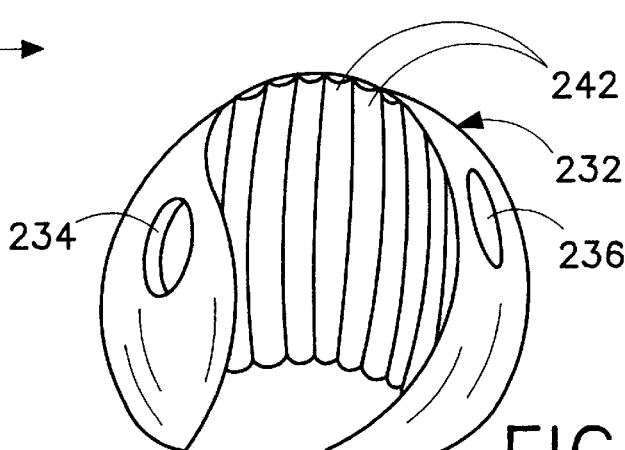
FIG. 15 is a schematic perspective view of the sensor vest of FIG. 14, showing the vest in an open configuration.

FIGS. 14 and 15 depict a specialized ultrasonic sensor web 232 in the form of a garment such as a vest. Sensor vest 232 has arm holes 234 and 236, a neck opening 238 and fasteners 240 for closing the vest about a patient. In addition, sensor vest 232 is provided with a plurality of elongate chambers 242 which receive fluid for expanding the vest into conformation with a patient's skin surface, thereby ensuring contact of the vest with a patient's skin surface and facilitating the transmission of ultrasonic pressure waves to and from ultrasonic transducers 244. FIG. 14 shows a computer 246, a video monitor 248 and a printer 250 used as described above.

Sensor vest 232 may be understood as a container assembly having fluid-filled chambers 242 with flexible inwardly facing walls (not separately designated) which conform to the patient.

Figure 16:
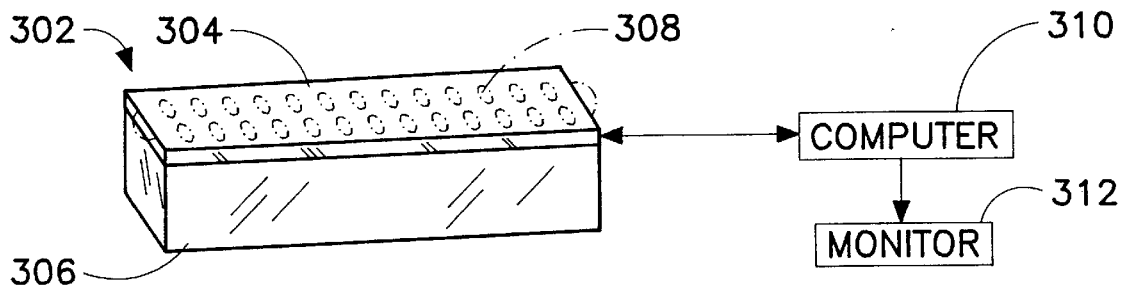
FIG. 16 is partially a schematic perspective view and partially a block diagram of an ultrasonic diagnostic imaging device in accordance with the present invention.
Figure 17:
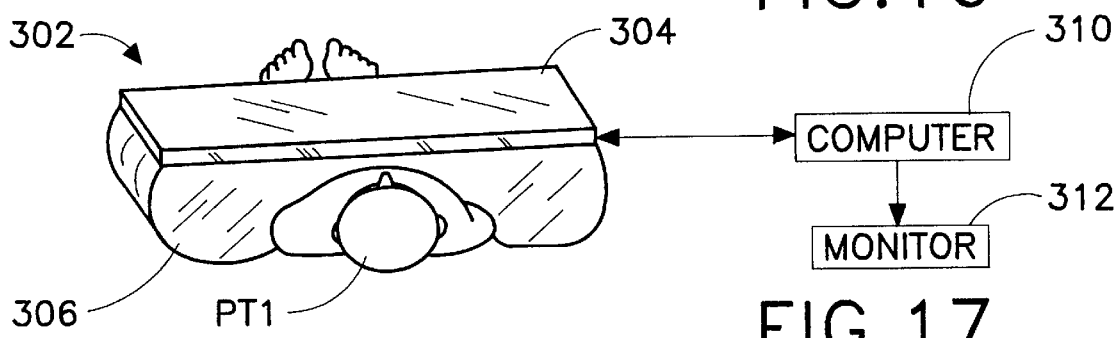
FIG. 17 is partially a schematic perspective view and partially a block diagram of the ultrasonic diagnostic imaging device of FIG. 16, showing the device in use with a patient.

As illustrated in FIG. 16, an ultrasonography apparatus comprises a container assembly 302 including a substantially rigid plate 304 attached to a flexible bladder or bag 306. Bladder or bag 306 is filled with a liquid and is sufficiently flexible to substantially conform to a patient when the container assembly 302 is placed onto a patient PT1, as illustrated in FIG. 17. A liquid may be deposited on the patient prior to the placement of container assembly 302 on patient PT1.

Plate 304 is provided with multiple ultrasonic pressure wave generators and detectors 308 as described above with respect to FIGS. 8 and 9 and FIGS. 14 and 15. Generators and detectors 308 are connected to a computer 310 having essentially the same functional structures and programming as computer 190 for implementing sequential generator energization and sequential detector sampling, as described above. Computer 310 is connected to a monitor 312 for displaying images of internal organs of patient PT1. Computer 310 has the capability of alternately displaying organ images from different angles, as discussed above.

Figure 18:
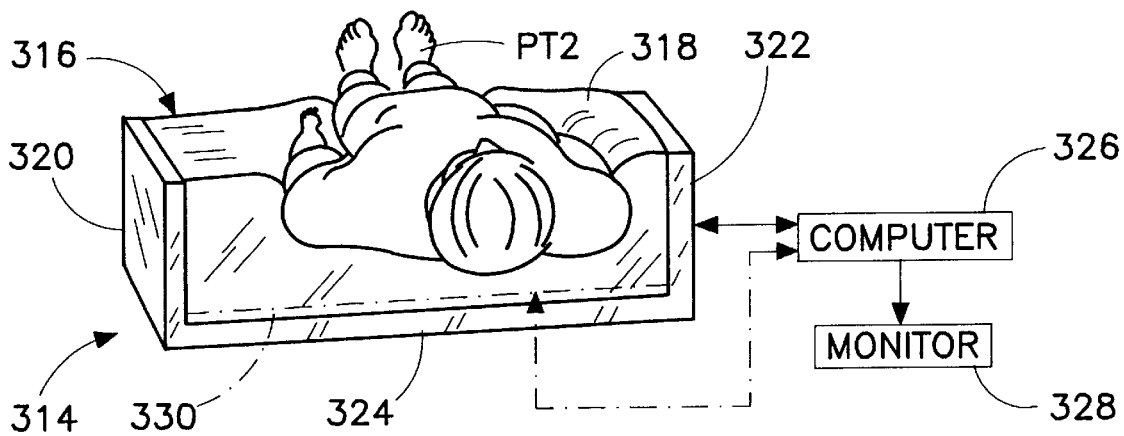
FIG. 18 is partially a schematic perspective view and partially a block diagram of another ultrasonic diagnostic imaging device in accordance with the present invention, showing the device in use with a patient.

FIG. 18 depicts another ultrasonography apparatus useful for both diagnostic investigations and minimally invasive surgical operations. The apparatus comprises a container assembly 314 which includes a fluid-filled sack or bag 316 for receiving a patient PT2. Sack or bag 316 include a flexible upper wall 318 which deforms to conform to the patient PT2 upon placement of the patient onto the bag. Bag 316 is supported on tow or more sides by substantially rigid walls or panels 320 and 322. Panels 320 and 322 are either integral with bag 316 or separable therefrom. Panels 320 and 322, as well as an interconnecting bottom panel 324, may be provided with multiple ultrasonic pressure wave generators and detectors (not shown) as described above with respect to FIGS. 8 and 9, FIGS. 14 and 15, and FIG. 16. These generators and detectors are connected to a computer 326 having essentially the same functional structures and programming as computer 190 for implementing sequential generator energization and sequential detector sampling, as described above. Computer 326 is connected to a monitor 328 for displaying images of internal organs of patient PT2. Computer 326 has the capability of alternately displaying organ images from different angles, as discussed above.

The ultrasonic pressure wave generators and detectors may be provided in a separate carrier 330 disposable, for example, between bottom panel 324 and bag 316, as shown in FIG. 18.

Figure 19:
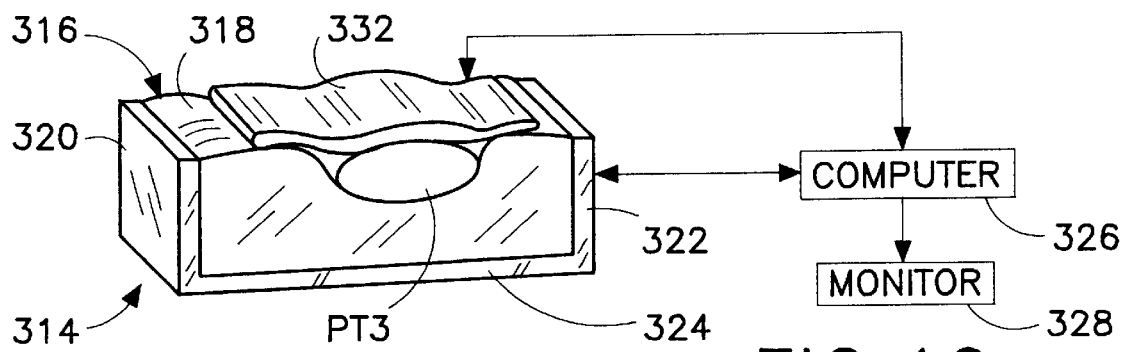
FIG. 19 is partially a schematic perspective view and partially a block diagram of the ultrasonic diagnostic imaging device of FIGS. 17 and 18, showing a modification of the device of those figures.

As illustrated in FIG. 19, the ultrasonography apparatus of FIG. 19 may be used in conjunction with a flexible web or cover sheet 332 identical to web 132, 150, or 206 (FIG. 8, 9, or 12). Web or cover sheet 332 is operatively connected to computer 326 for providing ultrasonically derived organ position and configuration data to the computer for displaying organ images on monitor 328. The use of web or sheet 332 enables the disposition of ultrasonic wave generators and detectors in a 360° arc about a patient PT3 (diagrammatically illustrated in FIG. 19), thereby facilitating image production. Where web or sheet 332 takes the form of web 206, the sheet is provided with apertures (see FIG. 12 and associated description) for enabling the introduction of minimally invasive surgical instruments into the patient PT3.

As discussed above, contact surfaces are advantageously wetted with liquid to facilitate ultrasonic pressure wave transmission over interfaces.

Although the invention has been described in terms of particular embodiments and applications, one of ordinary skill in the art, in light of this teaching, can generate additional embodiments and modifications without departing from the spirit of or exceeding the scope of the claimed invention. For example, in some applications, it may be advantageous to place the patient into a liquid bath, with ultrasonic signals being generated in the bath from container walls or panels. If a surgical procedure is to be implemented in this way, the patient must be stably supported in the bath so as to avoid floating. Floating of the patient, however, is not necessarily counterproductive where a diagnostic investigation is being conducted.

Accordingly, it is to be understood that the drawings and descriptions herein are proferred by way of example to facilitate comprehension of the invention and should not be construed to limit the scope thereof.

What is claimed is:

1. A medical system, comprising:
    a container assembly defining a fluid-filled chamber and including a substantially rigid panel defining an outer wall of said chamber, said container assembly having a flexible wall conformable to a patient;
    at least one electroacoustic transducer in operative contact with said container assembly for generating pressure waves in fluid disposed in said chamber;

an a-c current generator operatively connected to said transducer for energizing said transducer with an electrical signal of a pre-established ultrasonic frequency to produce a first pressure wave in said fluid in said chamber;

at least one acoustoelectric transducer in operative contact with said container assembly for receiving and sensing pressure waves traveling in said fluid in said chamber, at least one of said electroacoustic transducer and said acoustoelectric transducer being mounted to said substantially rigid panel; and analyzing means operatively connected to said acoustoelectric transducer for determining three-dimensional shapes of internal tissues of the patient by analyzing signals generated by said acoustoelectric transducer in response to second pressure waves produced at internal tissues of the patient in response to said first pressure wave and transmitted through said fluid in said chamber to said acoustoelectric transducer.

2. The system defined in claim 1, further comprising a video monitor linked to said analyzing means for displaying an image of said internal tissues.

3. The system defined in claim 2, further comprising a view selector operatively connected to said analyzing means and said video monitor for selecting said image from among a multiplicity of possible images of said internal tissues.

4. The system defined in claim 2, further comprising a filter stage operatively connected to said analyzing means and said video monitor for eliminating a selected organ from said image.

5. The system defined in claim 1 wherein said container assembly is in operative contact with a plurality of electroacoustic transducers disposed in a predetermined array, further comprising means for energizing said electroacoustic transducers in a predetermined sequence.

6. The system defined in claim 1 wherein said container assembly is in operative contact with a plurality of acoustoelectric transducers disposed in a predetermined array, further comprising means for receiving signals from said acoustoelectric transducers in a predetermined sequence.

7. A system for use in a medical operation, comprising:

a container assembly defining a fluid-filled chamber, said container assembly including a flexible wall partially defining said chamber, said flexible wall being conformable to and disposable in a pressure-wave-transmitting relationship with a patient, said container assembly including a panel provided with a plurality of apertures enabling traversal of said panel by a medical instrument so that a distal end of said medical instrument lies inside the patient while the patient is disposed in pressure-wave-transmitting contact with said fluid-filled chamber;

at least one electroacoustic transducer operatively mounted to said container assembly for generating pressure waves in the patient and in fluid disposed in said chamber;

an a-c current source operatively connected to said transducer for energizing said transducer with an electrical signal of a pre-established ultrasonic frequency to produce first pressure waves in the patient and in said fluid in said chamber;

at least one acoustoelectric transducer mounted to said container assembly for receiving and sensing pressure waves reflected from internal tissues of the patient; and analyzing means operatively connected to said acoustoelectric transducer for determining three-dimensional shapes of the internal tissues of the patient and a location of said distal end of said medical instrument by analyzing signals generated by said acoustoelectric transducer in response to the pressure waves reflected from the internal tissues of the patient and pressure waves produced at said distal end of said medical instrument in response to said first pressure waves.

8. The system defined in claim 7, further comprising a video monitor linked to said analyzing means for displaying an image of said internal organs.

9. The system defined in claim 8, further comprising a view selector operatively connected to said analyzing means and said video monitor for selecting said image from among a multiplicity of possible images of said internal organs.

10. The system defined in claim 8, further comprising a filter operatively connected to said analyzing means and said video monitor for eliminating a selected organ from said image.

11. The system defined in claim 7 wherein said container assembly includes a plurality of electroacoustic transducers dispoed in a predetermined array, further comprising means for energizing said electroacoustic transducers in a predetermined sequence.

12. The system defined in claim 7 wherein said container assembly includes a plurality of acoustoelectric transducers diposed in a predetermined array, further comprising means for receiving signals from said acoustoelectric transducers in a predetermined sequence.

13. A method for performing a medical operation, comprising:

providing (1) a medical instrument and (2) a container assembly defining a fluid-filled chamber, said container assembly including a flexible wall partially defining said chamber, said flexible wall being conformable to and disposable in pressure-wave-transmitting relationship with a patient, said container assembly having at least one electroacoustic transducer in operative contact with said chamber for generating pressure waves in the patient and in fluid in said chamber, said container assembly also having at least one acoustoelectric transducer in operative contact with said chamber for detecting pressure waves in the patient and in said fluid in said chamber;

disposing said container assembly and the patient proximately to one another so that said flexible wall substantially conforms to a skin surface of the patient to enable an acoustic or pressure-wave-transmitting relationship between said skin surface and said fluid in said chamber;

after disposition of said container assembly and the patient adjacent to one another, energizing said electroacoustic transducer with an electrical signal of a pre-established ultrasonic frequency to produce first pressure waves in said fluid in said chamber and in the patient;

inserting a distal end of said medical instrument into the patient so that said distal end of said medical instrument is disposed inside the patient while said flexible wall is disposed proximately to and substantially conforms to said skin surface; and automatically analyzing signals generated by said acoustoelectric transducer in response to second pressure waves produced at internal tissues of the patient and at said distal end of said medical instrument in response to said first pressure waves to thereby determine three-dimensional shapes of the internal tissues of the patient and a location of said distal end of said medical instrument relative to said internal tissues, thereby enabling a real time manipulation of said instrument to effectuate a medical operation on a selected one of said internal tissues and transmitted through said fluid in said chamber to said acoustoelectric transducer.

14. The method defined in claim 13 wherein said container assembly has a cover member diposed over the patient and provided with a plurality of apertures, the inserting of said medical instrument including passing said distal end of said medical instrument through one of said apertures.

15. The method defined in claim 14 wherein said medical instrument is a biopsy instrument.

16. The method defined in claim 15 wherein said medical operation, performable under real-time ultrasonically mediated observation, is taken from the group consisting essentially of breast biopsy, liver biopsy, kidney biopsy, and pleural biopsy.

17. The method defined in claim 14 wherein said medical instrument is taken from the group consisting essentially of drains, tubes, and catheters.

18. The method defined in claim 17 wherein said medical operation, performable under real-time ultrasonically mediated observation, is taken from the group consisting essentially of thoracentesis, abscess drainage, and placement of a tubular member inside said selected one of said internal organs.

19. The method defined in claim 14 wherein said medical instrument is a laparoscopic instrument.

20. The method defined in claim 13 wherein said container assembly is provided with a plurality of electroacoustic transducers disposed in a predetermined array, further comprising energizing said electroacoustic transducers in a predetermined sequence.

21. The method defined in claim 13 wherein said container assembly is provided with a plurality of acoustoelectric transducers disposed in a predetermined array, further comprising receiving signals from said acoustoelectric transducers in a predetermined sequence.

22. The method defined in claim 13, further comprising generating a video image of said internal organs and said distal end of said medical instrument in response to the analysis of signals generated by said acoustoelectric transducer.

23. The method defined in claim 22, further comprising selecting said image from among a multiplicity of possible images of said internal organs.

24. The method defined in claim 22, further comprising eliminating a selected organ from said image.

25. The method defined in claim 13, further comprising generating a printed image of said internal organs in response to the analysis of signals generated by said acoustoelectric transducer.

26. The method defined in claim 13, further comprising generating an additional signal encoding the determined three dimensional shapes of the internal organs and wirelessly transmitting said additional signal to a remote location.

* * * * *